United States Patent

Tashiro et al.

[11] Patent Number: 5,856,613
[45] Date of Patent: Jan. 5, 1999

[54] METHOD FOR PRODUCING β-METHYLNAPHTHALENE

[75] Inventors: Masaharu Tashiro; Toshio Tsutsui, both of Kanagawa; Osamu Kubota, Chiba; Shinichi Okada, Chiba; Toshihito Nakamura, Chiba, all of Japan

[73] Assignee: Fuji Oil Company Limited and Petroleum Energy Center, Tokyo, Japan

[21] Appl. No.: 719,990

[22] Filed: Sep. 25, 1996

[30] Foreign Application Priority Data

Sep. 27, 1995 [JP] Japan ................... 7-273458

[51] Int. Cl.⁶ ................ C07C 4/18; C07C 4/12
[52] U.S. Cl. ............ 585/485; 585/489; 585/26
[58] Field of Search ............... 585/485, 489, 585/26

[56] References Cited

U.S. PATENT DOCUMENTS

| | | | |
|---|---|---|---|
| 3,244,759 | 4/1966 | Schaeffer et al. | 585/480 |
| 3,865,891 | 2/1975 | Smirnov et al. | 585/485 |
| 3,929,619 | 12/1975 | Sinfelt et al. | 208/111 |
| 4,041,093 | 8/1977 | Smirnov et al. | 585/419 |
| 4,064,188 | 12/1977 | Smirnov et al. | 585/486 |
| 5,132,480 | 7/1992 | Tsutsui et al. | 585/489 |

*Primary Examiner*—Walter D. Griffin
*Attorney, Agent, or Firm*—Helfgott & karas, P C.

[57] ABSTRACT

The present invention provides a method for producing β-methylnaphthalene from an inexpensive and easily available feed oil. According to the invention, highly pure β-methylnaphthalene adequate for industrial use can be mass-produced at reduced costs. The method comprises catalytic hydrodealkylation of a feed oil containing an alkyl naphthalene having at least two methyl groups in the presence of a catalyst having at least one metal species of selected from the group consisting of vanadium (V), chromium (Cr), nickel (Ni), rhodium (Rh), platinum (Pt), iridium (Ir), and compounds of these metals as an active component and a carrier therefor containing at least one of alumina and silica as its primary component, with a hydrogen partial pressure of 1 to 50 kgf/cm$^2$, at a temperature of 450° C. to 650° C., and for a contact time of 3 to 35 seconds. The method of the invention is excellent in that it affords β-methylnaphthalene of a chemical grade with a high yield.

8 Claims, 2 Drawing Sheets

FEED OIL (RANGE OF BOILING POINT: 240 - 270°C)
β - METHYLNAPHTHALENE

PRODUCT OIL OF EXPERIMENT NO. 1
(RANGE OF BOILING POINT: 240 - 270°C)
β - METHYLNAPHTHALENE

METHOD FOR PRODUCING β-METHYLNAPHTHALENE

BACKGROUND OF THE INVENTION

1. Field of the Invention

The present invention relates to a catalytic hydrodealkylation method for producing β-methylnaphthalene, and more particularly to a method for producing β-methylnaphthalene of a chemical grade with a high yield from a feed oil containing an alkyl naphthalene having at least two methyl groups.

2. Related Art

β-Methylnaphthalene is a compound having a boiling point of 241.1° C. and a melting point of 34.4° C. At room temperature, it is a colorless solid in the form of crystals. It has conventionally been obtained, by means of being separated through crystallization operation from fractions having a boiling point around 240° C. of coal tar. Alternatively, it has been produced through vapor phase methylation reaction of naphthalene with methyl chloride, or through reduction of 2-methyl-1,4-naphthoquinone.

Recently, β-methylnaphthalene has become more noticeable and valuable as a starting material for producing polyesters in commercial base. However, conventional methods for producing β-methylnaphthalene, including separation from coal tar cannot supply it with sufficient amounts to comply with its demand. Moreover, β-methylnaphthalene prepared by such conventional methods is not satisfactory in terms of purity for industrial use.

In the other words, it is not technically and economically practicable to implement mass-production of β-methylnaphthalene of a chemical grade, i.e., β-methylnaphthalene having a purity of not less than 97–98% and containing reduced amounts of such non-hydrocarbon impurities as nitrogen, and sulfur by means of conventional experimental approaches for producing β-methylnaphthalene.

Accordingly, a new process applicable to industrial production of β-methylnaphthalene is necessary to comply with the requirements of supplying it at low costs.

It is also noted that, since β-methylnaphthalene was previously not demanded in great amounts as an industrial starting material, attempts to produce β-methylnaphthalene industrially have not attracted much attention to date. As a result, no attempts other than those experimental approaches mentioned above have been made for developing a new method for producing β-methylnaphthalene, especially that of chemical grade.

The present inventors searched an inexpensive feed oil which is readily available in petroleum and petrochemical industries and is replaceable for coal tar which has conventionally been used, and noticed an intermediate product obtained through various kinds of refining processes of a crude oil, particularly an intermediate fraction having a high content of naphthalene compounds, which is generated in catalytic-cracking heavy fractions of a crude oil to produce a gasoline stock.

The present inventors attempted to separate and collect β-methylnaphthalene directly from the intermediate fraction, and concluded that it has been technically difficult to obtain β-methylnaphthalene of a high grade having high purity and containing reduced amounts of non-hydrocarbon compounds such as sulfur-containing compounds and nitrogen-containing compounds, i.e., so-called β-methylnaphthalene of a chemical grade. This is firstly because such an intermediate fraction contains too small a ratio of β-methylnaphthalene against the whole naphthalene compounds to obtain it industrially, and secondly because, as shown in a gas chromatography chart of FIG. 2A, an intermediate fraction contains multi-fractional hydrocarbon components, including not only β-methylnaphthalene but also significant amounts of a variety of hydrocarbons having boiling points close to the boiling point of β-methylnaphthalene, as well as non-hydrocarbon impurities such as sulfur-containing compounds, nitrogen-containing compounds, etc.

Therefore, separation of β-methylnaphthalene from the intermediate fraction is technically very difficult and is not economically practicable.

In the course of research, the present inventors found out that β-methylnaphthalene was able to be effectively mass-produced with a significant reduction in the amount of impurities contained in β-methylnaphthalene product by catalytic hydrodealkylating of a feed oil containing alkyl naphthalenes such as the above-mentioned intermediate fraction. The present inventors conducted further research to conclude that this approach enables the conversion of a feed oil into an product oil containing an elevated content of β-methylnaphthalene and having such distillation properties that allow easy separation of β-methylnaphthalene of a high grade and that the approach is economically quite advantageous and attractive.

The present inventors examined known hydrodealkylation processes for alkyl aromatic compounds such as those described in Japanese Patent Application Laid-Open (kokai) Nos. 206686/1990, 298347/1990, and 304033/1990, to evaluate those applicabilities to β-methylnaphthalene production and found that these conventional hydrodealkylation processes are not applicable to the production of methylnaphthalenes having a specific methyl group, particularly β-methylnaphthalene, although these methods are capable of producing naphthalenes by complete dealkylation.

By the way, the invention disclosed in Japanese Patent Application Laid-Open No. 206686/1990, "Hydrodealkylation Process" has been filed to U.S. Patent Office and allowed as U.S. Pat. No. 5,132,480 dated Jul. 21, 1992, providing a process for catalytic hydrodealkylation of a feed oil having alkylaromatic hydrocarbons, wherein a two-column apparatus, one column for the catalytic hydrodealkylation and the other column for regeneration of the catalyst, is used, which comprises conducting the hydrodealkylation of a feed oil in a first column under the presence of a fluidized bed of a catalyst comprising substantially spherical particles having a weight mean diameter of 25 to 250 μm, an apparent density of 0.3 to 1.5 g/cm$^3$, a pore volume of 0.10 to 1.5 cm$^3$/g under the conditions maintained for the hydrodealkylation in the column of a total pressure of 2 to 30 kg/cm$^2$, a hydrogen partial pressure of 1.5 to 20 kg/cm$^2$ and a temperature of 350° to 700° C.

The invention disclosed in Japanese Patent Application Laid-Open No. 298347/1990, "Hydrodealkylation Process" has been filed to U.S. Patent Office and allowed as U.S. Pat. No. 5,053,574 dated Oct. 1, 1991, providing a process for catalytic hydrodealkylation of alkylaromatic hydrocarbons which comprises contacting an alkylaromatic compound under a hydrogen partial pressure of 1 to 50 kg/cm$^2$ and at a temperature of 450° to 700° C. with a catalyst which comprises porous alumina particles with coke deposited thereon in the pores, said alumina particles having a pore volume of 0.1 to 1.5 cm$^3$/g and a specific surface area of 5 to 500 m$^2$/g, the quantity of said coke being 1 to 30% by weight of said alumina particles, and the pore volume and the specific surface area of said catalyst being 0.05 to 1.5 cm$^3$/g and 1 to 500 m$^2$/g, respectively.

Japanese Patent Application No. 304033/1990 has disclosed a process for catalytic hydrodealkylation of alkylaromatic hydrocarbons which comprises contacting an alkylaromatic compound at a temperature of 450° to 680° C. under the presence of hydrogen with a catalyst which comprises vanadium (V) carried by alumina particles.

SUMMARY OF THE INVENTION

Realizing the above-mentioned difficulties involved in conventional experimental approaches for producing methylnaphthalene of a chemical grade, the present inventors performed intensive studies and experiments, and finally succeeded in the industrial production of β-methylnaphthalene of a chemical grade by using, as a feed oil, a light cycle oil (hereinafter referred to as LCO) containing dimethylnaphthalene and trimethylnaphthalene, and by applying specific reaction conditions to hydrodealkylation of the feed oil in the presence of a known catalyst.

LCO is a fraction having a boiling point range of 170°–370° C. obtained as a byproduct through catalytic cracking of heavy fractions of a crude oil in a fluidized catalyst bed to produce a gasoline stock. LCO contains a relatively large amount of alkyl naphthalenes with a wide variety. Preferably, light cycle oil or its equivalent used as a feed oil has a boiling point range of 200° to 320° C., and more preferably 230° to 300° C.

Accordingly, an object of the present invention is to provide a new method for producing β-methylnaphthalene with a high yield from an inexpensive source oil which is readily available in petroleum and petrochemical industries, thereby achieving mass-production of inexpensive β-methylnaphthalene capable of being used as an industrial starting material.

The method for producing β-methylnaphthalene according to the present invention comprises hydrodealkylation of a feed oil containing an alkyl naphthalene having at least two methyl groups in the presence of a catalyst having at least one metal species selected from the group consisting of vanadium (V), chromium (Cr), nickel (Ni), rhodium (Rh), platinum (Pt), iridium (Ir), and compounds of these metals as an active component and a carrier therefor containing at least one of alumina and silica as its primary component with a hydrogen partial pressure of 1–50 kgf/cm$^2$, at a temperature between 450° C. and 650° C., and for a contact time of 3–35 seconds.

DESCRIPTION OF PREFERRED EMBODIMENTS

Figure 1:
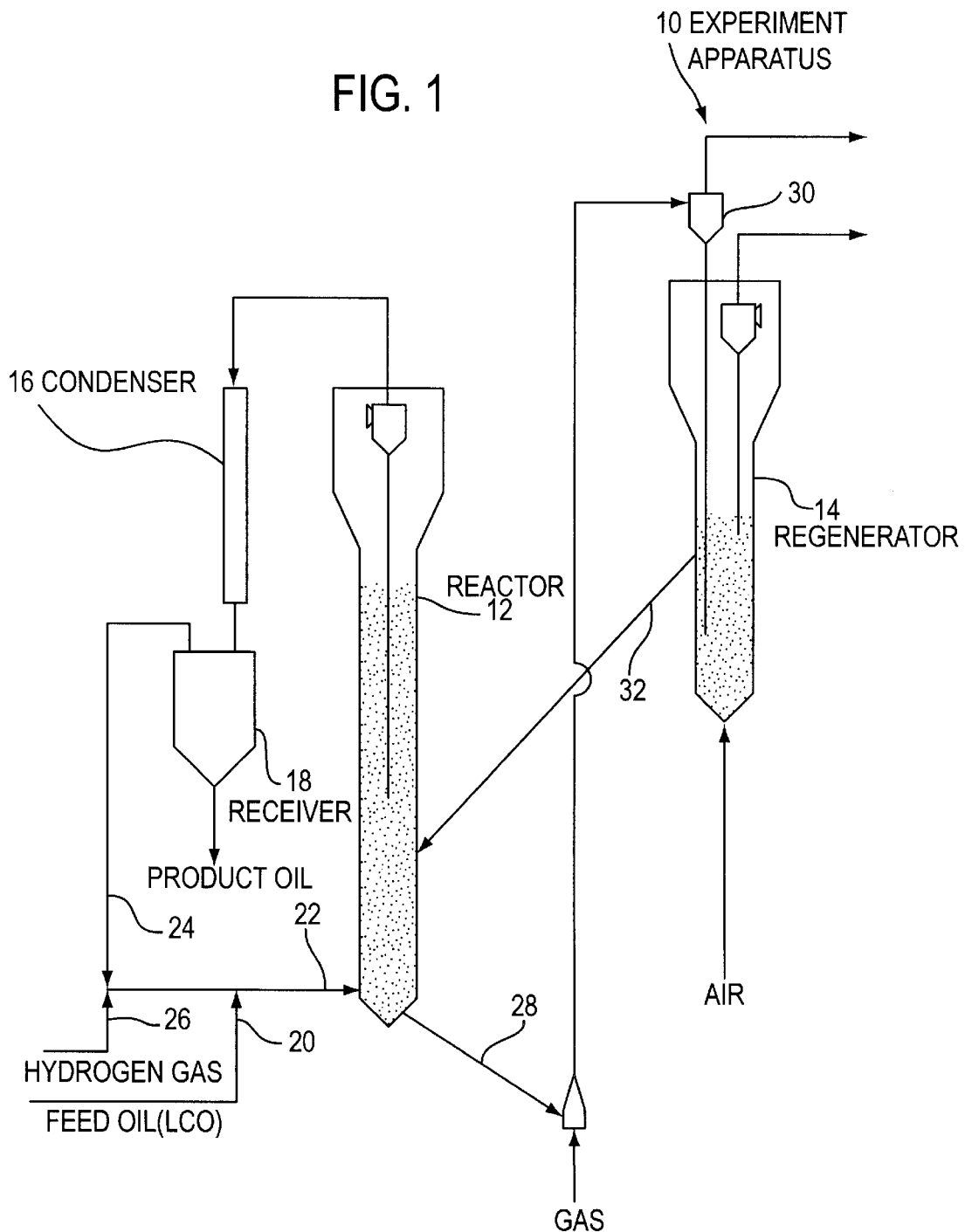
FIG. 1 is a schematic representation of an apparatus for performing reaction experiments.

The feed oil used in the method of the present invention is not particularly limited, so long as it contains an alkyl naphthalene having at least two methyl groups, e.g., dimethylnaphthalene and/or trimethylnaphthalene. In order to produce β-methylnaphthalene with a high yield, it is preferred that a feed oil containing not less than 10 mass % of at least either dimethylnaphthalene or trimethylnaphthalene be used. Examples of preferred feed oils include byproduct oils, such as light cycle oil (LCO) and heavy cycle oil (HCO), of catalytic cracking for heavy fractions of a crude oil, product oils of catalytic reforming for light fractions of a crude oil, byproduct oils of naphtha cracking, coal tar, and liquefied coal oils.

These feed oils may contain sulfur-containing compounds such as benzothiophene, nitrogen-containing compounds such as quinolines and indoles, and oxygen-containing compounds such as phenols, benzofurans, and dibenzofurans.

In the method of the present invention, the alkyl naphthalenes contained in the feed oil, while undergoing hydrodealkylation, are selectively converted into lower alkyl naphthalenes having a reduced number of alkyl groups as compared with the original alkyl naphthalenes. Also, part of α-methylnaphthalene is converted into β-methylnaphthalene through an isomerization reaction.

The catalyst used in the present invention may be a known one or a commercially available one, so long as it includes at least one metal species selected from the group consisting of vanadium (V), chromium (Cr), nickel (Ni), rhodium (Rh), platinum (Pt), iridium (Ir), and compounds of these metals as an active component and a carrier therefor containing at least one of alumina and silica as its primary component. Compounds of metals include oxides, sulfides, etc. of metals. Even when the catalyst further contains a small amount of molybdenum (Mo), rhenium (Re), and other trace metals in the form of a metal, a compound, etc., the catalytic activity is not affected adversely. The catalyst may further contain phosphorus (P) and other trace non-metal elements as well as various oxides, for instance such as oxides of barium (Ba), lanthanum (La), potassium (K) and calcium (Ca), including titania and magnesia.

For an example, taking an alumina carrier containing alumina as a primary component, it is preferred that approximately 10 mass % of silica be contained in the carrier so as to increase the thermal stability of catalyst particles.

The reactor for conducting the method of the present invention may be of a fixed bed type, a moving bed type, or a fluidized bed type. Alternatively, the reactor may have a catalyst bed of an arbitrary type other than the above.

Use of a fluidized bed reactor is preferred, firstly because it achieves an enhanced contact efficiency between a feed oil and a catalyst, secondly because it permits relatively feasible controllability and flexible change-ability for reaction conditions including the contact time and the reactor temperature, and thirdly because it can keep the reaction conditions be stable and uniform throughout the catalyst bed due to the particle mixing effect unique to a fluidized bed, even where an exothermic reaction such as a hydrodealkylating reaction is proceeding.

When a fluidized bed is used, the catalyst preferably takes the form of substantially spherical particles having a weight-mean diameter between 25 and 250 μm, and more preferably between 40 and 120 μm, and a bulk density between 0.3 and 1.5 g/cm$^3$, and more preferably between 0.4 and 1.3 g/cm$^3$. The catalyst with diminished catalytic activity is regenerated in a regenerator, using a gas containing molecular oxygen such as oxygen gas and air alone, or in coexistence with water vapor or CO$_2$. Regeneration of the catalyst is performed by completely or partially removing the coke formed on the catalyst by gasifying the coke at high temperature, preferably at 600°–1,000° C.

The partial pressure of hydrogen is usually 1 to 50 kgf/cm$^2$, preferably 2 to 30 kgf/cm$^2$, and more preferably 4 to 20 kgf/cm$^2$. If the partial pressure of hydrogen is equal to or less than 1 kgf/cm$^2$, formation of a coke on the catalyst is accelerated, thereby significantly decreasing the catalytic activity and the reaction rate of hydrodealkylation decreases. On the other hand, if the partial pressure of hydrogen is equal to or greater than 50 kgf/cm$^2$, the hydrogenating activity is too strong and excessively accelerates cracking of the feed oil, increasing the amount of gas produced to reduce the yield of β-methylnaphthalene.

The reaction temperature is specified to be between 450° and 650° C. for the reasons that hydrodealkylation does not sufficiently proceed at temperature lower than 450° C., resulting in reduction of yields of β-methylnaphthalene, and that hydrodealkylation proceeds excessively and undesirable side reactions are accelerated at temperature higher than 650° C., also resulting in reduction of yields of β-methylnaphthalene.

The contact time is specified to be between 3 and 35 seconds for the reasons that if the contact time is shorter than 3 seconds, hydrodealkylation does not sufficiently proceed, resulting in reduction of yields of β-methylnaphthalene, and that if the contact time is longer than 35 seconds, hydrodealkylation proceed excessively and undesirable side reactions are accelerated, also resulting in reduction of yields of β-methylnaphthalene.

According to preferred embodiments of the present invention, the contact time is between 5 and 30 seconds and the reaction temperature is between 500° and 630° C. By limiting reaction conditions in these ranges, proceeding of undesirable side reactions can be restricted to controllable extent and thus, yield of β- methylnaphthalene can be enhanced even more.

EXPERIMENTAL EXAMPLES

The present invention will next be described in more detail by way of experimental examples while referring to accompanying drawings.

Apparatus used for reaction experiment

FIG. 1 is a schematic drawing of the apparatus used in experiments for producing β-methylnaphthalene according to the present invention.

The apparatus 10 used for the reaction experiment is provided with a hollow cylindrical reactor 12 for performing hydrodealkylation of a feed oil, a hollow cylindrical regenerator 14 for regenerating catalyst whose catalytic activity has been diminished, a condenser 16 for condensing the product oil produced in the reactor 12, and a receiver 18 for receiving the product oil condensed and non-condensable gas in the condenser 16, and separating each other. A fluidized bed of catalyst is formed in both the reactor 12 and the regenerator 14.

The product oil in the receiver 18 can be easily separated into β-methylnaphthalene and others by use of a standard distillation operation.

Equipment of the apparatus 10 has the following dimensions:

Reactor 12:

Inner diameter: 8 cm

Height: 4.1 m

Amount of catalyst charged: 7.5 kg

Position of the supply port for a feed oil: 20 cm above the bottom

Regenerator 14:

Inner diameter: 8 cm

Height: 4.4 m

Amount of catalyst charged: 7.5 kg

The feed oil is fed through line 20 and line 22 to the lower section of the reactor 12, after being mixed with hydrogen gas. In the reactor 12, catalysts form a fluidized bed, having been fluidized by hydrogen gas. The feed oil undergoes hydrodealkylation in the presence of a catalyst to yield a gas abundantly containing β-methylnaphthalene converted from original alkyl naphthalenes. The generated gas thus leaves from the top of the reactor 12 and enters the condenser 16, together with un-reacted hydrogen gas. In the condenser 16, the generated gas is condensed into the product oil except hydrogen gas. The hydrogen gas and the condensed product oil are received by the receiver 18, where the hydrogen gas is separated. The separated hydrogen gas passes through line 24, and reenters the reactor 12, after joining with make-up hydrogen gas passing through line 26.

In the meantime, the catalyst with reduced activity due to carbon attached thereto leaves the bottom of the reactor 12 and enters the regenerator 14 after passing through line 28 and cyclone 30 by a gas flow transfer operation. In the regenerator 14, the carbon on the catalyst is burned by the air sent through the bottom of the regenerator 14, thereby the catalyst being regenerated. The thus regenerated catalyst is recycled to enter the reactor 12 via line 32.

Experiment Nos. 1–10:

Using the apparatus as described above, known catalysts A through D having compositions shown in Table 1, and LCO oils having properties shown in Table 2 as a feed oil, catalytic hydrodealkylation reactions were performed under a variety of conditions shown in Tables 3 and 4 to evaluate the present invention.

TABLE 1

| Catalyst | A | B | C | D |
|---|---|---|---|---|
| Active component | V | V | Cr | Ni |
| Content of active component (mass %) | 1.97 | 2.08 | 3.15 | 2.69 |
| Porosity (ml/g) | 0.47 | 0.59 | 0.90 | 0.90 |
| Specific surface area (m$^2$/g) | 263 | 215 | 239 | 239 |
| Weight-mean diameter (μm) | 63 | 61 | 70 | 70 |
| Bulk density (g/ml) | 0.71 | 0.65 | 0.48 | 0.48 |
| Carrier | Alumina carrier containing silica (10%) | | | |

Note:
The active components also include oxides of the indicated metals.

TABLE 2

| Composition of LCO | Feed oil 1 | Feed oil 2 | Feed oil 3 |
|---|---|---|---|
| Naphthalene (mass %) | 2.4 | 1.9 | 2.1 |
| β-MN (mass %) | 6.4 | 5.7 | 6.4 |
| α-MN (mass %) | 3.2 | 3.0 | 3.3 |
| DMN (mass %) | 11.9 | 13.6 | 12.7 |
| TMN (mass %) | 6.0 | 9.6 | 5.6 |
| Others (mass %) | 70.1 | 66.2 | 69.9 |
| Sulfur (mass %) | 0.3 | 0.06 | 0.06 |
| Nitrogen (mass ppm) | 230 | 260 | 220 |

Note:
α-MN: α-Methylnaphthalene
β-MN: β-Methylnaphthalene
DMN: Dimethylnaphthalene
TMN: Trimethylnaphthalene These abbreviations are also used in Tables 3 and 4.

TABLE 3

| Experiment No. | 1 | 2 | 3 | 4 | 5 | 6 |
|---|---|---|---|---|---|---|
| Catalyst | A | A | A | B | A | A |
| feed oil | 2 | 2 | 2 | 3 | 2 | 2 |
| Reaction temperature (°C.) | 600 | 570 | 530 | 630 | 500 | 480 |
| Contact time (sec) | 15.2 | 12.7 | 16.1 | 6.1 | 28.5 | 29.0 |
| Hydrogen partial pressure (kgf/cm$^2$) | 7.6 | 7.8 | 7.8 | 7.8 | 7.8 | 7.8 |
| Composition of Produced Oil | | | | | | |
| Naphthalene (mass %) | 15.6 | 10.6 | 7.6 | 19.8 | 12.8 | 10.5 |
| β-MN (mass %) | 9.2 | 10.9 | 11.1 | 7.7 | 11.3 | 9.8 |
| α-MN (mass %) | 4.2 | 5.2 | 5.3 | 3.7 | 5.3 | 4.8 |
| DMN (mass %) | 4.1 | 7.9 | 9.5 | 2.6 | 9.1 | 10.4 |
| TMN (mass %) | 0.4 | 1.2 | 1.2 | 0.3 | 1.1 | 1.6 |
| Others (mass %) | 22.4 | 27.4 | 39.3 | 22.3 | 41.0 | 36.2 |
| β-MN formation ratio (mass %) | 25.6 | 28.4 | 26.7 | 25.7 | 27.9 | 19.1 |
| β-MN production ratio (mass %) | 161 | 191 | 194 | 120 | 198 | 171 |
| Quality evaluation of produced oil | G | G | G | G | G | FG |
| Overall evaluation of produced oil | G | G | G | FG | G | FG |

TABLE 4

| Experiment No. | 7 | 8 | 9 | 10 | 11 | 12 | 13 |
|---|---|---|---|---|---|---|---|
| Catalyst | A | C | D | A | A | A | A |
| feed oil | 3 | 1 | 1 | 2 | 2 | 2 | 2 |
| Reaction temperature (°C.) | 670 | 600 | 550 | 600 | 530 | 500 | 430 |
| Contact time (sec) | 7.1 | 7.1 | 12.9 | 36.3 | 4.3 | 2.3 | 30.5 |
| Hydrogen partial pressure (kgf/cm$^2$) | 7.0 | 7.8 | 7.8 | 7.8 | 7.7 | 7.1 | 7.8 |
| Composition of Produced Oil | | | | | | | |
| Naphthalene (mass %) | 27.4 | 17.8 | 13.5 | 26.3 | 4.1 | 3.5 | 3.2 |
| β-MN (mass %) | 2.5 | 7.9 | 9.3 | 3.4 | 8.6 | 6.2 | 6.1 |
| α-MN (mass %) | 0.9 | 3.8 | 4.4 | 1.7 | 4.0 | 3.3 | 3.1 |
| DMN (mass %) | 0.4 | 3.3 | 5.0 | 0.6 | 11.6 | 12.0 | 13.2 |
| TMN (mass %) | 0.0 | 0.3 | 0.6 | 0.0 | 7.5 | 8.1 | 8.1 |
| Others (mass %) | 13.7 | 22.3 | 27.6 | 18.2 | 41.4 | 45.7 | 47.4 |
| β-MN formation ratio (mass %) | 7.3 | 25.4 | 28.3 | 9.2 | 13.7 | 3.0 | 3.0 |
| β-MN production ratio (mass %) | 39 | 123 | 145 | 59 | 150 | 108 | 107 |
| Quality evaluation of produced oil | G | G | G | G | G | NG | NG |
| Overall evaluation of produced oil | NG | FG | FG | NG | G | NG | NG |

The results of composition analyses of the produced oils are shown in Tables 3 and 4 under the heading of "Composition of Produced Oil". The constitution of each composition (mass %) was obtained based on the following equation:

Mass % of component X={(mass of component X contained in the product oil produced from 1 mass unit of a feed oil)/(mass of 1 mass unit of a feed oil)}×100

In Tables 3 and 4, the β-MN formation ratio (represented by %) denotes the conversion ratio of an alkylnaphthalene having two or more methyl groups into β-methylnaphthalene, (Here, β-MN is an abbreviation of β-methylnaphthalene.) and the β-MN production ratio (represented by %) denotes the ratio obtained based on the following equation:

β-MN production ratio={(mass of β-MN contained in the product oil produced from 1 mass unit of a feed oil)/(mass of β-MN contained in 1 mass unit of a feed oil)}×100

Accordingly, it is evaluated in Tables 3 and 4 that experimental cases providing higher β-MN production ratios are more preferable from viewpoint of the yield of production.

In Tables 3 and 4, the quality of produced oils was evaluated as "G" where a product oil provides a significantly high purity of β-methylnaphthalene when β-methylnaphthalene is separated by distillation from the product oil under the same distillation conditions; as "NG" when the purity is low; and as "FG" when the purity is intermediate. The overall evaluation of product oils indicates overall evaluation incorporating both of the evaluation of β-MN production ratio and the evaluation of quality of the product oil. The overall evaluation is indicated as G (good), FG (acceptable), and NG (not acceptable).

As shown in Tables 3 and 4, the reaction temperatures in Experiment Nos. 7 and 13 were 670° C. and 430° C., respectively, and the contact times in Experiment Nos. 10 and 12 were 36.3 seconds and 2.3 seconds, respectively. Thus, these Experiments, with either the contact time or the temperature being outside the range specified by the present invention, yielded low β-MN production ratios of 39%, 107%, 59%, and 108%, respectively. In other words, in these experiments, the amount of β-methylnaphthalene contained in the product oil produced from 1 mass unit of the feed oil is smaller than or substantially equal to the original amount of β-methylnaphthalene contained in 1 mass unit of the feed oil. This indicates that in these Experiment cases, reaction of hydrodealkylation proceeded to a much greater extent than the level required for formation of β-methylnaphthalene, resulting in completion of dealkylation to formation of naphthalene.

On the otherhand, in experiments other than Experiment Nos. 7, 10, 12, and 13, the β-MN production ratios were greatly higher than 100%, showing that β-methylnaphthalene was formed in amounts greater than the original amounts existing in the feed oil. Particularly, in Experiment Nos. 1 through 3, 5, 6, and 11, β-MN production ratios not less than 150% were obtained. The contact time and reaction temperature of these experiments were approximately 5 to 30 seconds and approximately 500° to 630° C. respectively.

Figure 2A:
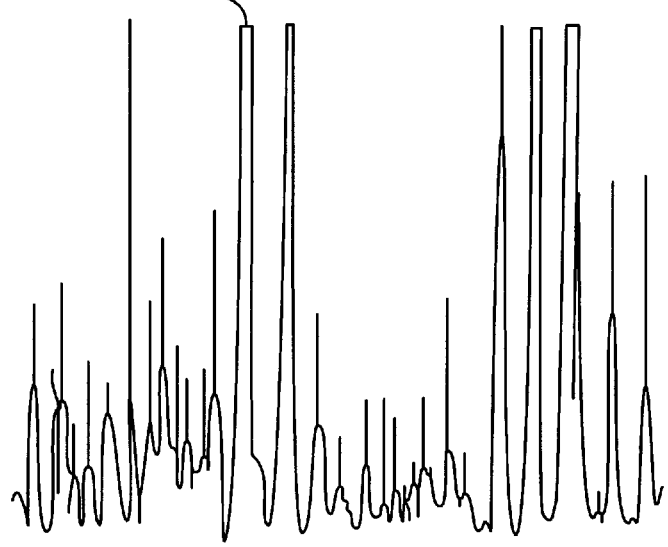
FIG. 2A and FIG. 2B are charts showing the results of gas chromatography of the feed oil and product oil, respectively.

The composition of the feed oil 2 (boiling point range: 240°–270° C.) is shown in the gas chromatography chart (FIG. 2A). From this chart, it is understood that the feed oil 2 contained, in addition to β-methylnaphthalene, a multiplicity of components each having a boiling point close to the boiling point of β-methylnaphthalene.

Figure 2B:
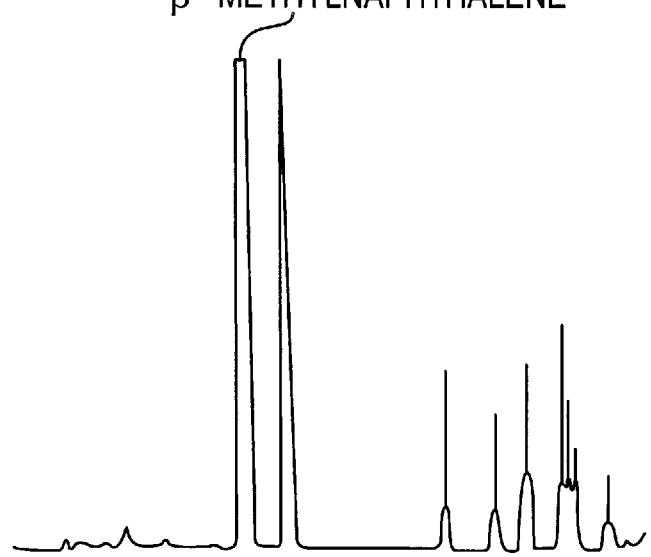

FIG. 2B is a chart showing the results of gas chromatography of the product oil (boiling point range: 240°–270° C.) obtained in Experiment No. 1. In this chart, the species of component having boiling points close to that of β-methylnaphthalene are greatly reduced. This demonstrates that separation of β-methylnaphthalene from the product oil in Experiment No. 1 is much more feasible than the feed oil 2 and thus β-methylnaphthalene of a high purity is obtainable.

As described above, in the present invention, hydrodealkylation is performed, using a known catalyst in the presence of hydrogen under specific conditions. As a result, it is feasible to produce β-methylnaphthalene having a high purity, i.e., β-methylnaphthalene of a chemical grade, with a high yield from an inexpensive feed oil containing alkyl naphthalenes.

Since the method of the present invention is capable of economically producing β-methylnaphthalene of a chemical grade from a feed oil which is inexpensive and readily available, β-methylnaphthalene having qualities desired for an industrial starting material can be mass-produced at reduced costs.

Since above embodiments are described only for examples, the present invention is not limited to such embodiments and it will be obvious for those skilled in the art that various modifications or alterations can be easily made based on the above embodiments within the scope of the present invention.

What is claimed is:

1. A method for producing β-methylnaphthalene comprising catalytic hydrodealkylation of a feed oil containing at least one compound selected from the group consisting of sulfur-containing compounds, nitrogen-containing compounds, and oxygen-containing compounds as impurities in addition to an alkyl napthalene having at least two methyl groups in the presence of a catalyst having at least one metal selected from the group consisting of vanadium (V), chromium (Cr), nickel (Ni), rhodium (Rh), platinum (Pt), iridium (Ir), and compounds of said metals as an active component and a carrier therefor containing at least one of alumina and silica as its primary component, under the operating conditions with a hydrogen partial pressure of 1 to 50 kgf/cm$^2$, at a temperature of 450° to 650° C., and for a contact time of 3 to 35 seconds.

2. The method as defined in claim 1, wherein the contact time is between 5 and 30 seconds and the reaction temperature is between 500° and 630° C.

3. The method as defined in claim 1, wherein the feed oil contains 10 mass % or more of at least one of dimethylnaphthalene and trimethylnaphthalene.

4. The method as defined in claim 2, wherein the feed oil contains 10 mass % or more of at least one of dimethylnaphthalene and trimethylnaphthalene.

5. The method as defined in claim 3, wherein the feed oil is light cycle oil or its equivalent, which is produced in catalytic cracking of heavy fractions of a crude oil and has a boiling point range of 200° to 320° C.

6. The method as defined in claim 4, wherein the feed oil is light cycle oil or its equivalent, which is produced in catalytic cracking of heavy fractions of a crude oil and has a boiling point range of 200° to 320° C.

7. The method as defined in claim 3 wherein the feed oil is light cycle oil or its equivalent which is produced in catalytic cracking of heavy fractions of a crude oil and has a boiling point range of 230° to 300° C.

8. The method as defined in claim 4 wherein the feed oil is light cycle oil or its equivalent which is produced in catalytic cracking of heavy fractions of a crude oil and has a boiling point range of 230° to 300° C.

* * * * *